(12) United States Patent
Forsberg

(10) Patent No.: US 6,595,952 B2
(45) Date of Patent: Jul. 22, 2003

(54) GUIDE CATHETER WITH BACKUP SUPPORT SYSTEM

(75) Inventor: Andrew Forsberg, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 66 days.

(21) Appl. No.: 09/754,713

(22) Filed: Jan. 4, 2001

(65) Prior Publication Data

US 2002/0087143 A1 Jul. 4, 2002

(51) Int. Cl.[7] ............ A61M 31/00; A61M 29/00; A61M 25/00
(52) U.S. Cl. ............ 604/93.01; 604/104; 604/525
(58) Field of Search ............ 604/6.16, 507, 604/508, 509, 93.01, 96.01, 104, 523, 524, 525, 532; 606/194

(56) References Cited

U.S. PATENT DOCUMENTS

| | | | |
|---|---|---|---|
| 4,169,464 A | 10/1979 | Obrez | 128/657 |
| 4,781,682 A | 11/1988 | Patel | 604/96 |
| 4,784,639 A | 11/1988 | Patel | 604/53 |
| 4,813,930 A | 3/1989 | Elliott | 604/53 |
| 4,813,938 A | 3/1989 | Raulerson | 604/158 |
| 4,820,271 A | 4/1989 | Deutsch | 604/99 |
| 4,832,028 A | 5/1989 | Patel | 128/344 |
| 4,909,787 A | 3/1990 | Danforth | 604/95 |
| 5,000,743 A | 3/1991 | Patel | 606/194 |
| 5,016,640 A | 5/1991 | Ruiz | 128/658 |
| 5,045,072 A | 9/1991 | Castillo et al. | 604/280 |
| 5,098,412 A * | 3/1992 | Shiu | 600/585 |
| 5,122,125 A | 6/1992 | Deuss | 604/282 |
| 5,163,928 A | 11/1992 | Hobbs et al. | 604/281 |
| 5,171,232 A | 12/1992 | Castillo et al. | 604/280 |
| 5,188,619 A | 2/1993 | Myers | 604/280 |
| 5,195,990 A * | 3/1993 | Weldon | 604/280 |
| 5,203,776 A | 4/1993 | Durfee | 604/264 |
| 5,231,994 A | 8/1993 | Harmjanz | 128/772 |
| 5,299,574 A * | 4/1994 | Bower | 600/435 |
| 5,306,262 A * | 4/1994 | Weldon | 604/264 |
| 5,306,263 A * | 4/1994 | Voda | 600/435 |
| 5,322,509 A | 6/1994 | Rickerd | 604/53 |
| 5,348,545 A | 9/1994 | Shani et al. | 604/281 |
| 5,354,271 A | 10/1994 | Voda | 604/49 |
| 5,401,258 A * | 3/1995 | Voda | 604/523 |
| 5,445,625 A | 8/1995 | Voda | 604/281 |
| 5,462,561 A | 10/1995 | Voda | 606/144 |
| 5,497,774 A | 3/1996 | Swartz et al. | 128/658 |
| 5,658,263 A | 8/1997 | Dang et al. | 604/280 |
| 5,662,621 A | 9/1997 | Lafontaine | 604/281 |
| 5,680,873 A | 10/1997 | Berg et al. | 128/772 |
| 5,800,413 A | 9/1998 | Swartz et al. | 604/280 |
| 5,868,700 A | 2/1999 | Voda | 604/49 |
| 5,891,057 A | 4/1999 | Chaisson et al. | 600/585 |
| 6,083,213 A | 7/2000 | Voda | 604/500 |
| 6,086,548 A | 7/2000 | Chaisson et al. | 600/585 |
| 6,110,163 A | 8/2000 | Voda | 604/523 |
| 6,120,495 A | 9/2000 | Voda | 604/523 |

FOREIGN PATENT DOCUMENTS

| | | |
|---|---|---|
| JP | 3-228773 | 10/1991 |
| WO | WO 92/12754 | 8/1992 |
| WO | WO 93/21983 | 11/1993 |

* cited by examiner

Primary Examiner—Ehud Gartenberg
Assistant Examiner—John K Fristoe, Jr.
(74) Attorney, Agent, or Firm—Crompton, Seager & Tufte, LLC

(57) ABSTRACT

An intravascular catheter (e.g. guide or diagnostic catheter) that includes a specially designed distal tip to provide enhanced back-up support. The distal tip (e.g., distal 2 cm of the shaft) has a lateral extent or profile (e.g., wave shape) that is larger than the lumen of the coronary artery adjacent the ostium when the tip is in a relaxed state. The over-sized lateral extent causes the distal tip to frictionally engage the coronary artery and anchor within the ostium. The lateral extent or profile of the distal tip may be decreased by inserting a guide wire therethrough to facilitate insertion of the distal tip into the ostium. After the distal tip is inserted into the ostium, the guide wire may be removed to allow the lateral extent of the distal tip to increase and thereby anchor the distal tip in the ostium.

15 Claims, 4 Drawing Sheets

GUIDE CATHETER WITH BACKUP SUPPORT SYSTEM

FIELD OF THE INVENTION

The present invention generally relates to intravascular catheters. More specifically, the present invention relates to intravascular coronary guide catheters.

BACKGROUND OF THE INVENTION

Intravascular guide catheters are commonly used to guide therapeutic and diagnostic devices to remote locations in a patient's vascular system. For example, coronary guide catheters are commonly used to position a balloon catheter in a patient's coronary artery to perform a percutaneous transluminal coronary angioplasty (PTCA) procedure. An example of a conventional PTCA guide catheter 10 is illustrated in FIG. 1. The PTCA guide catheter 10 includes an elongate shaft 12 having a proximal end, a distal end and a lumen extending therethrough. A hub 14 is connected to the proximal end of the elongate shaft 12. The distal end of the elongate shaft 12 includes a preformed curved portion 16 and a distal tip portion 18, the geometry of which may vary depending on the particular vascular anatomy being navigated.

In a typical PTCA procedure, the distal end of the guide catheter 10 is inserted into the patient's femoral artery near the groin, and is advanced up the descending aorta 20, across the aortic arch 22, and down the ascending aorta 28 until the distal tip 18 is seated in the ostium of the right coronary artery (RCA) 24 or the left coronary artery (LCA) 26 as illustrated in FIG. 2. Usually, approximately 1 mm–5 mm of the distal tip 18 is seated in the ostium. Once the distal tip 18 is seated in the ostium, a therapeutic or diagnostic device (e.g., a balloon catheter, an atherectomy catheter, an IVUS catheter, etc.) may be inserted into the lumen of the guide catheter 10, advanced therethrough, and navigated through the lumen of the coronary artery 24/26.

Because the lumen of the coronary artery 24/26 is often restricted or tortuous, it is often difficult to navigate intravascular devices therethrough, particularly when accessing distal vascular sites. When resistance to advancement through the lumen of the coronary artery 24/26 is encountered, the physician typically applies additional pushing force to the intravascular device in an attempt to overcome the resistance. If significant resistance is encountered, the distal tip 18 of the guide catheter 10 tends to back-out of the ostium. When the distal tip 18 backs-out of the ostium, it is difficult if not impossible to advance the intravascular device any further and it is likely that the intravascular catheter will prolapse in the lumen of the ascending aorta 28.

To address this problem, some physicians attempt to deep-seat the distal tip 18 in the ostium. However, this deep-seating technique often causes misalignment between the lumen of the guide catheter 10 and the lumen of the coronary artery 24/26, thereby compromising advancement of intravascular devices therethrough. In addition, deep-seating the distal tip 18 may cause unnecessary trauma to the inside surface of the coronary artery 24/26, potentially exacerbating the underlying clinical condition being treated and/or potentially causing additional clinical problems.

As an alternative to deep-seating, various means to provide a back-up support have been proposed in the prior art. For example, U.S. Pat. No. 4,813,930 to Elliott and U.S. Pat. No. 5,098,412 to Shiu propose mechanisms which utilize a structure to brace against the wall of the ascending aorta 28 opposite the ostium of the coronary artery 24/26 being accessed. Alternatively, U.S. Pat. No. 4,832,028 to Patel and U.S. Pat. No. 5,122,125 to Deuss propose an inflatable balloon at the distal end of the guide catheter to anchor the distal tip in the ostium of the coronary artery being accessed. Although each of these prior art designs may provide back-up support to the guide catheter and thereby resist back-out from the ostium, each of the proposed embodiments involve unnecessarily complexed designs which may compromise performance and handling of the guide catheter and which most certainly will increase the manufacturing cost of the guide catheter. Accordingly, there is a substantial unmet need for a guide catheter which provides enhanced back-up support without compromising performance and without substantially increasing design complexity.

SUMMARY OF THE INVENTION

To avoid the suboptimal performance associated with deep-seating conventional guide catheters and the unnecessarily complex design of the balloon-anchor guide catheters of the prior art, the present invention provides a guide catheter that includes a specially designed distal tip to frictionally engage a coronary artery adjacent its ostium. The intravasclar catheter of the present invention, which may comprise a guide catheter or a diagnostic catheter, for example, is elegantly simple in design and does not compromise performance while providing enhanced back-up support.

In an exemplary embodiment, the present invention provides an intravascular coronary catheter, such as a guide catheter or a diagnostic catheter, including a distal tip (e.g., distal 2 cm of the shaft) that has a lateral extent or profile that is larger than the lumen of the coronary artery adjacent the ostium when the distal tip is in a relaxed state such that the distal tip frictionally engages the coronary artery. The frictional engagement with the coronary artery anchors the distal tip in the ostium and thereby provides back-up support. Preferably, the distal tip is wave-shaped in two or three dimensions. The lateral extent or profile of the distal tip may be decreased (i.e., straightened) by inserting a guide wire to facilitate insertion of the distal tip into the ostium. After the distal tip is inserted into the ostium, the guide wire may then be removed to allow the lateral extent of the distal tip to increase and thereby anchor the distal tip in the coronary artery.

After the distal tip is anchored in the ostium, a balloon catheter or other intravascular device may be inserted through the guide catheter and into the lumen of the coronary artery. If resistance to advancement through the lumen of the coronary artery is encountered, the anchored distal tip of the guide catheter provides sufficient back-up support to the balloon catheter in order to overcome the resistance to advancement. If significant resistance is encountered, it is contemplated that by applying additional pushing force to the balloon catheter, the lateral extent of the distal tip may be further increased to further engage the coronary artery and thereby provide additional back-up support.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
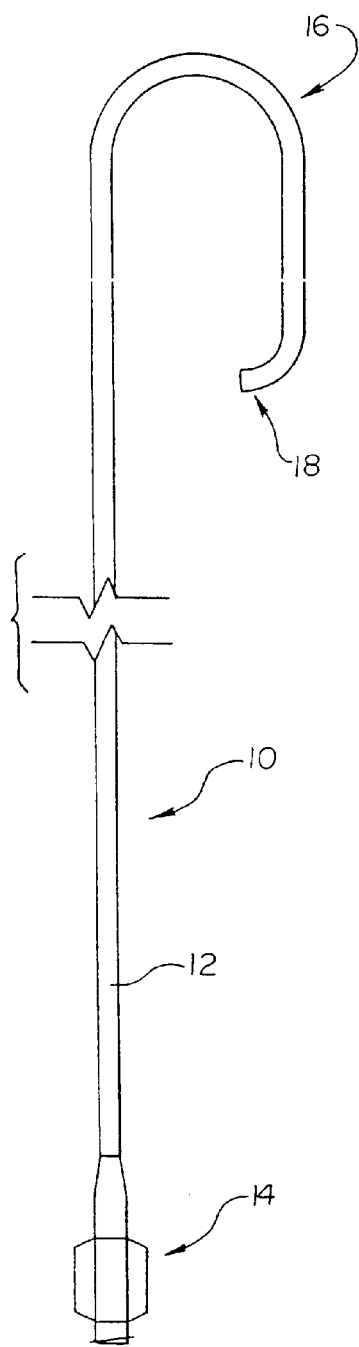
FIG. 1 is a plan view of a conventional PTCA guide catheter.
Figure 2:
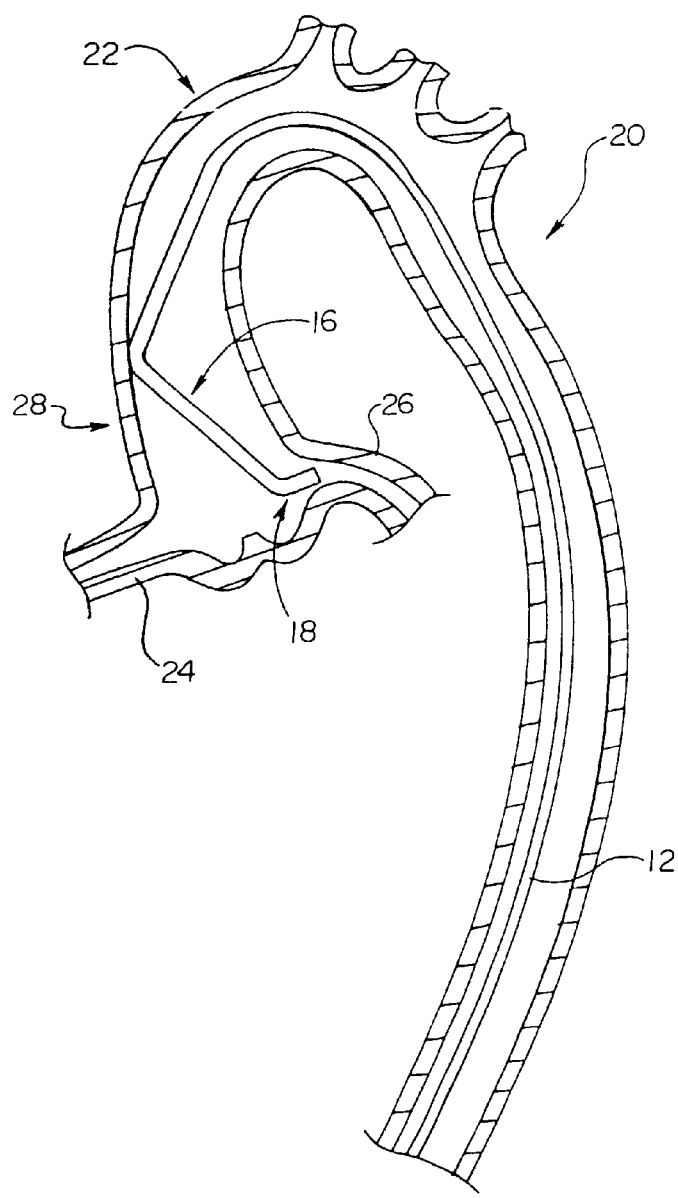
FIG. 2 is a cross-sectional view of a portion of the aortic vasculature and a portion of the coronary vasculature with the conventional guide catheter of FIG. 1 disposed therein.
Figure 3:
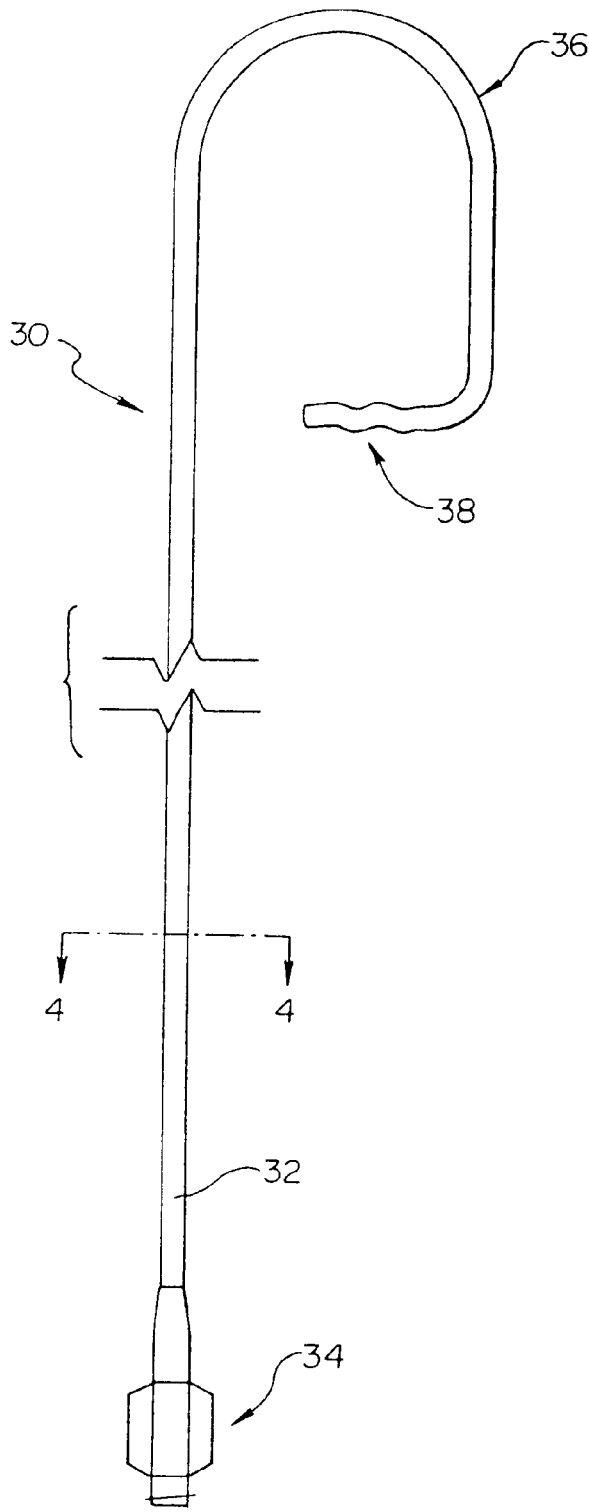
FIG. 3 is a plan view of a guide or diagnostic catheter in accordance with an embodiment of the present invention.

Refer now to FIG. 3 which illustrates catheter 30 in accordance with an exemplary of the present invention. Catheter 30 may be virtually any intravascular coronary catheter such as a guide or diagnostic catheter. For sake of simplicity and illustration, catheter 30 is described in terms of a guide catheter.

Guide catheter 30 includes an elongate shaft 32 having a proximal end, a distal end and a lumen 40 extending therethrough. A conventional manifold 34 is connected to the proximal end of the elongate shaft 32. The elongate shaft 32 includes a distal curved portion 36. The distal curved portion 36 may comprise a wide variety of shapes and curve styles depending on the particular vascular geometry being navigated. The elongate shaft 32 also includes a distal tip 38. The distal tip 38 generally has a lateral extent or profile that is larger than the lumen of the coronary artery being accessed when the tip 38 is in a relaxed state such that the distal tip frictionally engages the ostium of the coronary artery, as will be discussed in greater detail with reference to FIGS. 5A and 5B.

Figure 4:
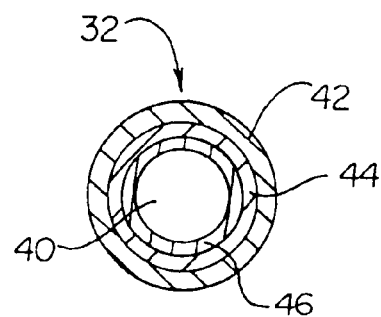
FIG. 4 is a cross-sectional view taken along line 4—4 in FIG. 3.

Refer now to FIG. 4 which illustrates a cross-sectional view of the elongate shaft 32 taken along line 4—4 in FIG. 3. The elongate shaft 32 may comprise a wide variety of conventional catheter constructions including the multi-layer construction illustrated in FIG. 4. The elongate shaft 32 may comprise, for example, an inner lubricious polymeric layer 46, a wire braid reinforcement layer 44, and a polymeric outer layer 42. Those skilled in the art will recognize that the design and construction of the shaft 32 may vary depending on the desired performance characteristics of the guide catheter 30.

Figure 5A:
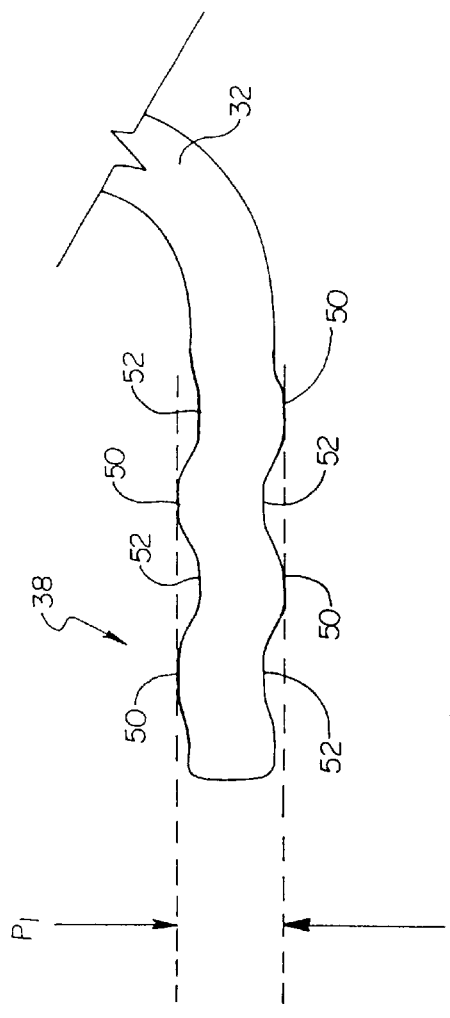
FIG. 5A is a detailed view of the distal tip of the catheter illustrated in FIG. 3 shown in the relaxed state.
Figure 5B:
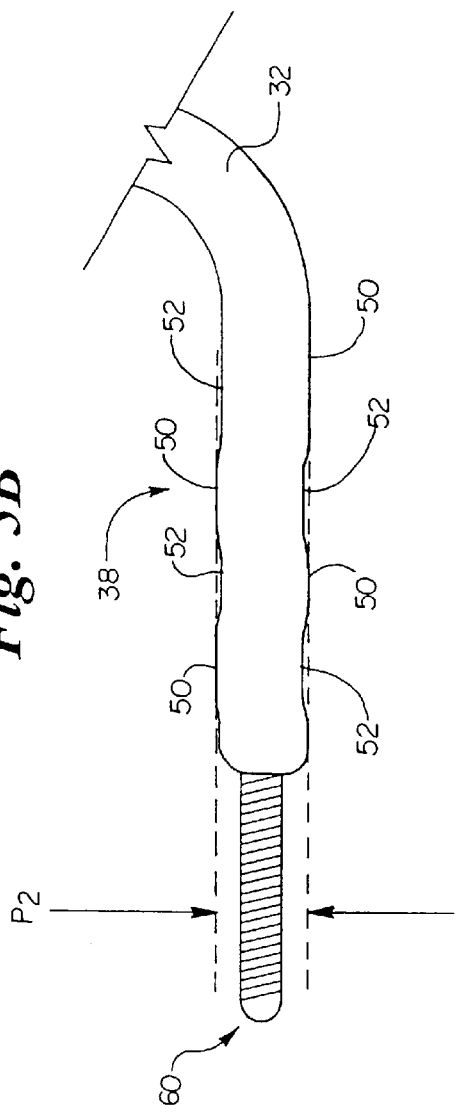
FIG. 5B is a detailed view of the distal tip of the catheter illustrated in FIG. 3 shown with a guide wire extending therethrough.

Refer now to FIGS. 5A and 5B which illustrate detailed views of the distal tip 38 of the guide catheter 30. FIG. 5A illustrates the distal tip 38 in the relaxed state, and FIG. 5B illustrates the distal tip 38 in the stressed state as induced by a guide wire 60 extending therethrough. In the relaxed state, the distal tip 38 has a lateral extent or profile $P_1$. The relaxed profile $P_1$ is greater than the inside diameter of the coronary artery being accessed adjacent its ostium such that the distal tip 38 frictionally engages the inside surface of the coronary artery. The stressed profile $P_2$ is less than the inside diameter of the coronary artery being accessed such that the distal tip 38 may be easily inserted into the ostium thereof using guide wire 60.

To provide a lateral extent or profile $P_1$ that is greater than the size of the lumen of the coronary artery being accessed, the distal tip 38 may have a wave-shape defining a plurality of peaks 50 and valleys 52. The distance between the furthermost apexes of the peaks 50 defines the lateral extent or profile $P_1$. The wave geometry may be symmetrical or asymmetrical and may be two or three dimensional.

The wave geometry of the distal tip 38 may be made by thermoforming techniques. For example, a wave-shaped mandrel may be inserted into the lumen 40 of the distal tip 38 followed by the application of heat for a period of time. After cooling, the mandrel may be removed leaving the wave-shape formed in the distal tip 38. Preferably, the shaft diameter of the distal tip 38 does not vary despite the wave-shape. In particular, the distance between the peak 50 and the valley 52 corresponds to the diameter of the remainder of the elongate shaft 32.

As mentioned previously, the distal tip 38 has a lateral extent or profile $P_1$ in the relaxed state that is larger than the lumen of the coronary artery being accessed. To facilitate insertion of the distal tip 38 into the ostium of the coronary artery being accessed, a guide wire 60 may be inserted into the lumen 40 and through the distal tip 38 to a decreased lateral extent or profile $P_2$. The decreased lateral extent or profile $P_2$ is preferably less than the size of the lumen of the coronary artery being accessed such that the distal tip is easily inserted therein. Upon removal of the guide wire 60 from the lumen 40 of the distal tip 38, the distal tip 38 elastically returns to its relaxed profile $P_1$ to frictionally engage the coronary artery adjacent the ostium. The distal tip is sufficiently flexible and elastic such that the lateral extent or profile of the distal tip 38 may elastically change between the relaxed profile $P_1$ and the stressed profile $P_2$. By frictionally engaging the coronary artery adjacent the ostium, the distal tip 38 anchors the guide catheter 30 therein thereby providing enhanced back-up support.

The wave-shaped distal tip 38 may have a length between 0.5 cm and 2.5 cm, a nominal shaft diameter between 4 F and 11 F, and a relaxed profile $P_1$ between 1.1 and 2.0 times the nominal shaft diameter, depending on the size of the coronary lumen and the desired amount of frictional engagement. Preferably, the length of the curved portion of the distal tip 38 is 1.5 cm or less to avoid the possible adverse effects of deep-seating the guide catheter 30 in the coronary artery.

Figure 6:
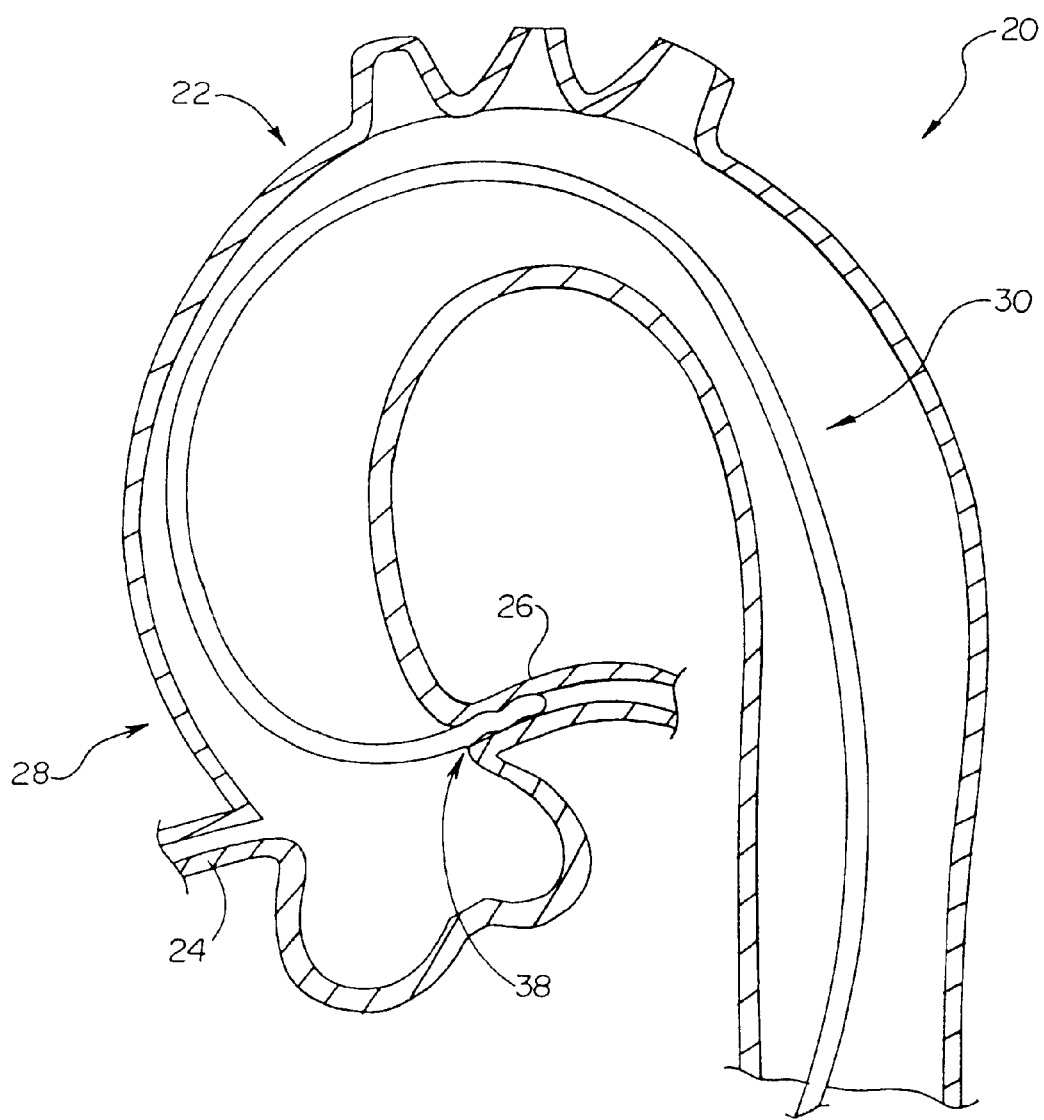
FIG. 6 is a cross-sectional view of a portion of the aortic vasculature and a portion of the coronary vasculature with the catheter of FIG. 3 disposed therein.

Refer now to FIG. 6 which illustrates the guide catheter 30 disposed in the aortic and coronary vasculature of a patient. In use, the guide catheter 30 is inserted into the patient's vascular system utilizing conventional techniques until the distal tip 38 is adjacent the ostium leading to the right coronary artery 24 or left coronary artery 26. The guide wire 60 is typically disposed in the lumen 40 during this process such that the lateral extent or profile of the distal tip 38 is reduced as illustrated in FIG. 5B. The distal end of the guide wire 60 and the distal tip 38 of the guide catheter 30 are inserted into the ostium of the coronary artery 26 being accessed. Once the distal tip 38 extends into the lumen of the coronary artery 26, the guide wire 60 is retracted in the proximal direction allowing the distal tip 38 to return to its relaxed (expanded) state as illustrated in FIG. 5A. In the relaxed or expanded state, the distal tip 38 frictionally engages the inside surface of the coronary artery 26 to anchor the guide catheter 30 therein.

Once the guide catheter 30 is positioned as illustrated in FIG. 6, another intravascular device such as a balloon catheter may be inserted into the lumen 40 of the guide catheter 30 and navigated into the lumen of the coronary artery 26. If substantial resistance to advancement through the lumen of the coronary artery is encountered, additional pushing force may be applied to the balloon catheter to cause the lateral extent of the distal tip 38 to increase and thereby further engage the coronary artery 26. By this method, the guide catheter 30 provides enhanced back-up support to successfully navigate through restrictions and tortuous vasculature as may be encountered in PTCA procedures.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular catheter providing access to a lumen of a coronary artery having an ostium, the catheter comprising an elongate shaft having a proximal portion and a distal tip, the distal tip having a lateral profile that is larger than the lumen of the coronary artery adjacent the ostium when the tip is in a relaxed state such that the distal tip frictionally engages the coronary artery, the distal tip having a lateral profile that is smaller than the lumen of the coronary artery adjacent the ostium when the tip is in a stressed state.

2. An intravascular catheter as in claim 1, wherein the elongate shaft includes a single lumen.

3. An intravascular catheter as in claim 1, wherein the distal tip has a shaft diameter, and wherein the shaft diameter of the distal tip is less than the lateral profile of the distal tip.

4. An intravascular catheter as in claim 1, wherein the distal tip is wave-shaped.

5. An intravascular catheter as in claim 4, wherein the wave-shaped distal tip is two dimensional.

6. An intravascular catheter as in claim 4, wherein the wave-shaped distal tip is three dimensional.

7. An intravascular catheter as in claim 4, wherein the distal tip is sinusoid-shaped.

8. An intravascular catheter system for providing access to a lumen of a coronary artery having an ostium, the system comprising:

a catheter comprising an elongate shaft having a proximal portion, a distal tip and a lumen extending therethrough, the distal tip having a lateral profile that is larger than the lumen of the coronary artery adjacent the ostium when the tip is in a relaxed state such that the distal tip frictionally engages the coronary artery, the distal tip having a lateral profile that is smaller than the lumen of the coronary artery adjacent the ostium when the tip is in a stressed state; and a guide wire disposed in the lumen of the shaft, wherein the lateral profile of the distal tip decreases when the guide wire extends therethrough.

9. A method of accessing a lumen of a coronary artery having an ostium, the method comprising the steps of:

providing an intravascular catheter comprising an elongate shaft having a proximal portion, a distal tip and a lumen extending therethrough, the distal tip having a lateral profile that is larger than the lumen of the coronary artery adjacent the ostium when the distal tip is in a relaxed state and a lateral profile that is smaller than the lumen of the coronary artery adjacent the ostium when the tip is in a stressed state; and inserting the distal tip into the ostium such that the distal tip frictionally engages the coronary artery.

10. A method as in claim 9, further comprising the steps of:

providing a guide wire; and inserting the guide wire into the lumen of the shaft and through the distal tip such that the lateral profile of the distal tip decreases.

11. A method as in claim 10, wherein the step of inserting the guide wire to decrease the lateral profile of the distal tip is performed prior to the step of inserting the distal tip into the ostium.

12. A method as in claim 11, further comprising the step of:

retracting the guide wire from the distal tip such that the lateral profile of the distal tip increases.

13. A method as in claim 12, wherein the step of retracting the guide wire from the distal tip such that the lateral profile increases is performed subsequent to the step of inserting the distal tip into the ostium.

14. A method as in claim 13, further comprising the steps of:

providing an intravascular device; and inserting the intravascular device into the lumen of the catheter and into the lumen of the coronary artery.

15. A method as in claim 14, further comprising the steps of:

advancing the intravascular device through the lumen of the coronary artery; and upon encountering resistance to advancement through the lumen of the coronary artery, applying additional pushing force to the intravascular device to cause the lateral profile of the distal tip of the catheter to increase and thereby further engage the coronary artery adjacent the ostium.

* * * * *